United States Patent
Lan et al.

(10) Patent No.: US 12,252,840 B2
(45) Date of Patent: Mar. 18, 2025

(54) TEXTILE FORMULATION AND PRODUCT WITH ODOR CONTROL

(71) Applicant: MICROBAN PRODUCTS COMPANY, Huntersville, NC (US)

(72) Inventors: Tian Lan, Huntersville, NC (US); Brian Patrick Aylward, Concord, NC (US); Tiannan Chen, Dewitt, MI (US); Karen Terry Welch, Kannapolis, NC (US)

(73) Assignee: MICROBAN PRODUCTS COMPANY, Huntersville, NC (US)

( * ) Notice: Subject to any disclaimer, the term of this patent is extended or adjusted under 35 U.S.C. 154(b) by 0 days.

(21) Appl. No.: 18/385,645

(22) Filed: Oct. 31, 2023

(65) Prior Publication Data
US 2024/0060229 A1    Feb. 22, 2024

Related U.S. Application Data

(60) Continuation of application No. 16/175,214, filed on Oct. 30, 2018, now Pat. No. 11,840,797, which is a division of application No. 14/947,605, filed on Nov. 20, 2015, now abandoned.

(60) Provisional application No. 62/111,834, filed on Feb. 4, 2015, provisional application No. 62/084,928, filed on Nov. 26, 2014.

(51) Int. Cl.
*D06M 11/45* (2006.01)
*A61L 2/18* (2006.01)

(52) U.S. Cl.
CPC ............... *D06M 11/45* (2013.01); *A61L 2/18* (2013.01)

(58) Field of Classification Search
CPC ......... A61K 8/26; A61Q 15/00; D06M 11/45; D06M 2101/32; D06M 16/00; D06M 23/08; A61L 2/16; A61L 2/18; A61L 2101/00; A61L 2202/26
USPC ........................................ 442/121, 123, 124
See application file for complete search history.

(56) References Cited

U.S. PATENT DOCUMENTS 3,013,901 A * 12/1961 Bugosh ................... B32B 27/00
                                                            428/404
3,650,968 A    3/1972 Hoffman
4,180,467 A   12/1979 Barth
(Continued)

FOREIGN PATENT DOCUMENTS

AU    2006297826 A1    4/2007
EP       480244 A2     4/1992
(Continued)

OTHER PUBLICATIONS

Dispersal and Dispal, https://products.sasol.com/pic/products/home/grades/US/5disperal-and-dispal/index.html, (Year: 2022).*
(Continued)

*Primary Examiner* — Matthew D Matzek
(74) *Attorney, Agent, or Firm* — Shumaker, Loop & Kendrick, LLP

(57) ABSTRACT

A textile formulation adapted to impart an odor-controlling property to a textile material. The textile formulation is an odor capturing formulation comprising a carrier and an odor capturing agent. The odor capturing agent is a liquid dispersible boehmite. An odor absorbing article and a method of treating the odor absorbing article is also provided.

19 Claims, 1 Drawing Sheet

(56) References Cited

U.S. PATENT DOCUMENTS

| | | | |
|---|---|---|---|
| 4,891,150 A | 1/1990 | Gross |
| 4,919,829 A | 4/1990 | Gates |
| 5,017,656 A | 5/1991 | Bopp |
| 5,089,258 A | 2/1992 | Zaid |
| 5,095,694 A | 3/1992 | Shekleton et al. |
| 5,122,407 A | 6/1992 | Yeo |
| 5,509,941 A | 4/1996 | Gurley |
| 5,539,930 A | 7/1996 | Sesselman |
| 4,749,603 B2 | 6/1998 | Esaki |
| 5,781,216 A | 7/1998 | Haruta |
| 5,790,987 A | 8/1998 | Sesselmann |
| 5,800,922 A | 9/1998 | Anderson |
| 5,891,391 A | 4/1999 | Fore |
| 5,928,720 A | 7/1999 | Kuhn |
| 6,221,951 B1 | 4/2001 | de Wit et al. |
| 6,245,693 B1 | 6/2001 | Gagliardi |
| 6,348,423 B1 | 2/2002 | Griffiths |
| 6,562,743 B1 | 5/2003 | Cook |
| 6,652,845 B2 | 11/2003 | Hu |
| 6,686,008 B1 | 2/2004 | Merlin |
| 6,747,186 B2 | 6/2004 | Shimizu |
| 6,764,969 B1 | 7/2004 | Kuhn |
| 6,767,553 B2 | 7/2004 | Sun |
| 6,861,520 B1 | 3/2005 | Todd |
| 6,906,010 B2 | 6/2005 | Hoy |
| 6,998,155 B2 | 2/2006 | Haggquist |
| 7,101,924 B2 | 9/2006 | Von Schmittou |
| 8,574,683 B2 | 5/2013 | Hamed |
| 8,629,070 B2 | 1/2014 | Oles |
| 8,771,661 B2 | 7/2014 | MacDonald |
| 9,315,937 B2 | 4/2016 | Gedanken |
| 2004/0052957 A1* | 3/2004 | Cramer ............. D06M 10/00 427/280 |
| 2005/0084412 A1 | 1/2005 | MacDonald |
| 2005/0142966 A1 | 6/2005 | Quincy, III |
| 2005/0145577 A1 | 8/2005 | Jenkins |
| 2006/0037150 A1 | 2/2006 | Offord |
| 2006/0138380 A1 | 6/2006 | Kulke |
| 2006/0147698 A1 | 7/2006 | Carroll |
| 2007/0010150 A1 | 1/2007 | Fang |
| 2007/0020451 A1 | 1/2007 | Hamed |
| 2007/0062882 A1 | 3/2007 | Adams |
| 2007/0071933 A1 | 3/2007 | Gavelli |
| 2007/0118562 A1 | 5/2007 | Edwards et al. |
| 2008/0164439 A1 | 7/2008 | Fang |
| 2008/0171068 A1 | 7/2008 | Wyner |
| 2008/0185333 A1 | 8/2008 | Gibson |
| 2009/0081440 A1 | 3/2009 | Bringley |
| 2009/0149097 A1 | 6/2009 | Effenberger |
| 2009/0257923 A1 | 10/2009 | Seto |
| 2009/0311293 A1 | 12/2009 | Fratini |
| 2010/0129593 A1 | 5/2010 | Rempt |
| 2010/0189595 A1 | 7/2010 | Webster |
| 2010/0206029 A1 | 8/2010 | Sutton |
| 2010/0221486 A1 | 9/2010 | Nonninger |
| 2010/0267881 A1 | 10/2010 | Tiefenbruck |
| 2011/0252970 A1 | 10/2011 | Jones |
| 2011/0263174 A1 | 10/2011 | Ketzer |
| 2011/0308386 A1 | 12/2011 | Claraq |
| 2012/0164097 A1 | 6/2012 | Huchel |
| 2012/0164903 A1 | 6/2012 | Wardle |
| 2012/0308369 A1 | 12/2012 | Maheshwari |
| 2013/0000052 A1 | 1/2013 | Peeters |
| 2013/0095274 A1 | 4/2013 | Jones |
| 2013/0139327 A1 | 6/2013 | Sieben |
| 2014/0076797 A1 | 3/2014 | Jo |
| 2014/0121272 A1 | 5/2014 | Smith |
| 2014/0248812 A1 | 9/2014 | Lang |
| 2015/0056102 A1 | 2/2015 | Yamada |
| 2015/0272235 A1 | 10/2015 | Ko |
| 2015/0352392 A1 | 12/2015 | Kaiser |

FOREIGN PATENT DOCUMENTS

| | | |
|---|---|---|
| EP | 1379725 B1 | 1/2004 |
| GB | 2396841 A | 7/2004 |
| JP | 2003832 A2 | 1/1977 |
| WO | 2001094687 A2 | 12/2001 |
| WO | 2002091977 A1 | 11/2002 |
| WO | 2003092885 A1 | 11/2003 |
| WO | 2007040623 A1 | 4/2007 |
| WO | 2011008204 A1 | 1/2011 |
| WO | 2013095289 A1 | 6/2013 |
| WO | 2014125920 A1 | 8/2014 |

OTHER PUBLICATIONS

Pural Catapal, High-Purity Alumina Hydrates, Sasol Performance Chemicals from https://sasoldcproducts.blob.core.windows.net/documents/Product%20Brochures/EU_Inorganics_PURAL%20CATAPAL%20Overview.pdf (Year: 2023).

Dis Peral and Dis Pal, https://products.sasol.com/pic/products/home/grades/US/5disperal-and.

Exley, Christopher; "Does antiperspirant use increase the risk of aluminium-related disease, including Alzheimer's disease?"; Molecular Medicine Today, Mar. 1998, pp. 107-109; Elsevier Science Ltd.; United Kingdom; all enclosed pages cited.

Sciessent, Sciessent Lava, http://www.sciessent.com/sciessent-lava-technology, accessed website on Jun. 6, 2018.

* cited by examiner

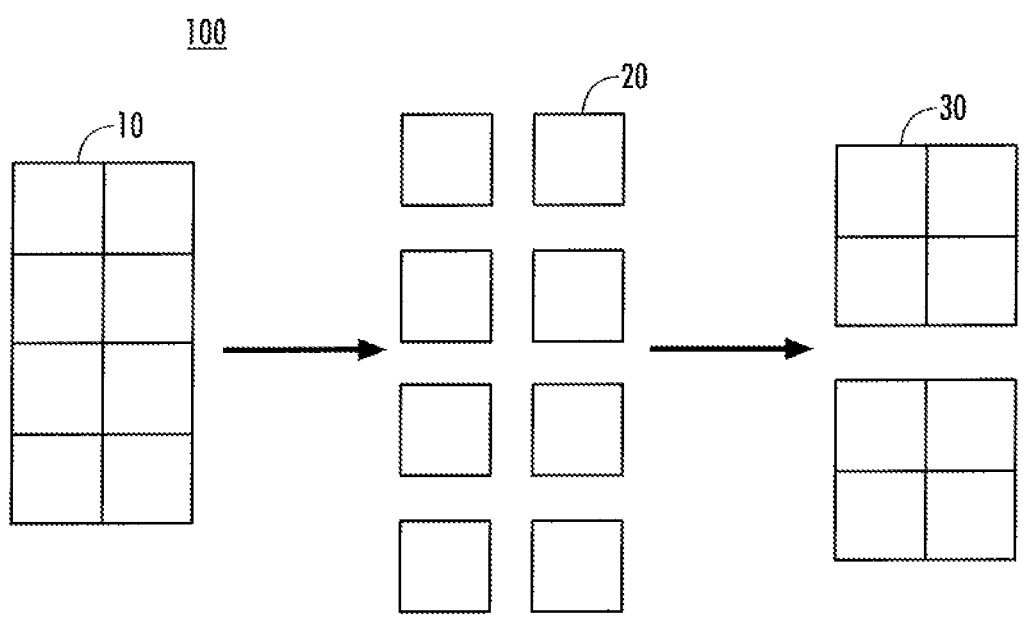

TEXTILE FORMULATION AND PRODUCT WITH ODOR CONTROL

CROSS-REFERENCE TO RELATED APPLICATIONS

This application claims priority from U.S. non-provisional patent application Ser. No. 16/175,214, filed on Oct. 30, 2018, which claims priority from U.S. non-provisional patent application Ser. No. 14/947,605, filed on Nov. 20, 2015, which claims priority from U.S. provisional patent application Ser. No. 62/084,928, filed on Nov. 26, 2014, and from U.S. provisional patent application Ser. No. 62/111,834, filed on Feb. 4, 2015, in the United States Patent and Trademark Office. The disclosures of which are incorporated herein by reference in their entireties.

FIELD OF THE INVENTION

The present disclosure relates to textile materials and, more particularly, to a formulation adapted to impart an odor-controlling property to a textile material treated therewith.

BACKGROUND OF THE INVENTION

Microbes exist everywhere in the modern world. While some are beneficial to humans and the environment, others have significant negative consequences for contaminated articles as well as the persons, animals and ecological members coming in contact with them.

A lesser yet significant concern is placed on malodor arising from garments and other textiles goods after being worn. Malodor is created, or increased, when the user is active.

For this reason, there is a need for textile goods, and preferably active wear and sporting apparel, resistant to the development of offensive odors.

One approach has been the treatment of textile materials or substrates to impart an odor-absorbing property thereto. While such treatments can be effective for some articles, they can be overwhelmed under conditions such as high activity.

Such approaches also have suffered from poor durability, especially when repeatedly laundered.

Despite technical activity and advancements in this area, there remains a need for a textile treatment able to prevent the development of malodor.

It further would be advantageous for the odor-controlling property to be durably associated with the textile article, such that it may continue to provide odor control for the useful life of the textile material.

Textile materials used in apparel tend to generate unpleasant odors due to the metabolic action of microorganisms on human sweat. This causes the breakdown of larger molecules present in sweat, which releases volatile small molecules such as isovaleric acid. Using antimicrobials sometimes is insufficient to control odors in textiles. It would be more efficient to apply odor capturing agents by themselves or along with antimicrobials to control the odor. The current odor capturing product for textile finishing treatment is found not durable to home laundries by itself. A binder or cross-linker has to be used along with the odor capturing agents to afford durability. Binders or cross-linkers bring negative effects to textile material properties such as softness or colorfastness. Therefore it is the objective of this invention to develop an effective odor capturing finishing composition, which is durable to home launderings, preferably without using a binder or a cross-linker once the composition is applied onto to textile materials

SUMMARY OF THE INVENTION

The present invention relates to a textile formulation adapted to impart an odor-controlling property to a textile material. The textile formulation is an odor-capturing formulation comprising an alumina, preferably a liquid dispersible or soluble alumina as an odor capturing agent. In an aspect of the invention, the odor capturing formulation does not require use of either a binder or a cross-linker. Thus, the formulation of the present invention is particularly suitable to impart a durable odor capturing property to a textile material.

In an aspect of the invention, the odor capturing formulation contains an odor control chemistry that when dispersed in deionized water has a dispersed particle size of 10000 nanometers or less, preferably 500 nanometers or less, more preferably 100 nanometers or less.

In another aspect of the invention, a method of making the odor capturing formulation is provided.

In another aspect of the present invention, a treated textile material is provided having a durable odor capturing property.

In still yet another aspect of the present invention, a method of treating a textile material is provided.

Further areas of applicability of the present invention will become apparent from the detailed description provided hereinafter. It should be understood that the detailed description and specific examples, while indicating the preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, which are not necessarily to scale, wherein:

FIG. 1 is a diagram illustrating a proposed mechanism for the present invention.

DETAILED DESCRIPTION OF EMBODIMENTS OF THE INVENTION

In accordance with the invention, a formulation is provided that comprises an alumina as an odor capturing agent. As a feature of the invention, the formulation does not require use of either a binder or a cross-linker to impart a durable odor capturing property to a textile material.

In an aspect of the invention, the odor capturing agent is an alumina, preferably a liquid or water dispersible or soluble alumina. The liquid dispersible or soluble alumina acts as the odor capturing or absorbing agent. A wide variety of forms of alumina can be used for the invention. The term "alumina," as used herein, refers to alumina as well as alumina derivatives.

In a preferred aspect of the invention, alumina suitable for use in the invention has the following generic molecular formula:

Where
X is oxygen O
Y is hydrogen H
a, b, and c are each integers, where a is in a range of 1 to 5, b is in a range of 1 to 10, and c is in a range of 0 to 20.

The above molecular formula may or may not encompass single element impurities or a combination of impurities introduced into the alumina either from the source of the alumina origination or during the manufacturing process of alumina product.

Examples of alumina suitable for the present invention include, but are not limited to, natural occurring alumina such as gibbsite ($Al(OH)_3$), boehmite ($\gamma$-AlO(OH)), diaspore ($\alpha$-AlO(OH)), and Kaolinite ($Al_2O_3$, $2SO_2 \cdot 2H_2O$). Aluminas ($Al_2O_3$) with various crystalline structures derived from these natural raw materials through phase transition process may also be suitable. Among them boehmite, AlOOH, is preferred. Also, preferred is a non-fibrous boehmite.

Even though the natural occurring aluminas and their derivatives can be used, synthetic aluminas including its derivatives are preferred. For example, synthetic boehmite can be synthesized through an intermediate aluminum hydroxide or alkoxide at high pH and elevated temperature via gelation process. Alumina with various phases or crystal structures can be used, including but not limited to, a, e, 13, and y structures.

Modifications using encapsulation or doping methods with various elements such as silica, zinc, and titanium may also be useful to further improve the odor capturing performance of the alumina of the present invention.

Boehmite may be used either in powder form or in a form of a pre-dispersed liquid product. Particularly preferred are boehmite powders. If powder is used, the powder can be liquid (such as water) dispersible by itself or with the aid of an additional dispersant.

Examples of commercially available boehmite powders are those manufactured by Sasol under the trade names DISPERAL and DISPAL. Both dry powder forms of the product and pre-dispersed liquid version of the alumina are suitable for use in the present invention.

The powder version of the boehmite is dispersible or soluble in water and may subsequently be applied onto a textile material in a typical textile wet manufacturing process. The boehmite is used to treat the textile and provide odor capture without 3-g lycidyloxypropyltrimethoxysilane (GPTMS) finishing, or without GPTMS finishing.

The powder alumina and liquid dispersible or soluble alumina are available in different particle sizes. Powder alumina particles normally have much larger size than the same particles dispersed in water and this is because the powder particle is in a agglomerated state where small and individual particles join together to form large particles. Once being dispersed in deionized water, the agglomerated alumina dissociates and disintegrates into small particles. The dispersed particle sizes particularly suitable for use in the present invention are in a range of 10000 nanometers or less, preferably 500 nanometers or less, and more preferably 100 nanometers or less when dispersed in deionized water.

For application such as a treatment onto a textile material, powder alumina is first dispersed or dissolved in water or solvent either by itself or with another beneficial textile finishing agent such as a moisture management agent or a softener and then is applied onto textile material in a typical or customary textile wet finishing process such as padding and exhaustion. After the finishing process, the textile material is cured at preferred elevated temperatures to finish the treatment process. In the process, the alumina is essentially locked into the textile material to provide continuous odor capturing effect to the textile material. The odor capturing effect is also durable to launderings.

Referring to the FIGURES, FIG. 1 is a diagram illustrating a proposed mechanism 100 in accordance with aspects of the present invention. Dry powder alumina 10 is first dispersed in water with mixing in the formulation process of the present invention. During the dispersing process, the aggregated alumina powder is subjected to chemical and mechanical forces. These forces cause larger alumina powder particles to dissociate into smaller primary aggregates of dispersed alumina 20.

For purposes of a textile finishing process, the formulation of the present invention is first diluted in water and then applied homogenously onto textile substrate via an application process such as a padding process or exhaustion. Under suitable conditions of pressure and temperature, the small, primary alumina aggregates easily penetrate the structure of the textile material deeply and either becomes trapped in small pores present within the structure of the textile material or create a durable coating on the surface of the textile material.

After padding, the textile materials impregnated with the formulation of the present invention undergo a curing process to be dried. During the curing process, the alumina particles join together to form larger particles of dried/cured alumina 30. The final size of the alumina aggregates within the textile material is to be determined and limited by the size of the pore in the textile material where the alumina particles aggregate. Presumably the alumina aggregate grows in size until the particle fills the room of the pore. Since the particle size of the alumina matches up to the size of the pore, it is difficult for the alumina to escape the cage during a textile laundering process. Essentially the alumina is locked into the textile substrate and becomes durable to laundry without a binder or without a cross-linker.

A method of making the formulation of the present invention comprises dispersing the dry powder form of the alumina in an aqueous media or using a soluble alumina in an aqueous media. The dispersing process may use a mixing tank or vessel equipped with a mixer in the middle of the tank. In most cases, water is charged into the tank first and the mixing is initiated. The alumina powder is charged slowly in the tank with mixing. The mixing is continued until the alumina powder is preferably completely and evenly dispersed in water. If there are other components or additional additives involved in the formulation process, those components or other additives can also be added into the tank with mixing either prior to or following the addition of alumina powder. In a preferred aspect of the invention, the mixing process is continued until the final formulation is completely homogenous.

The alumina formulation may be applied onto a textile material by any finishing process available in a textile finishing manufacturing setup. For example, foam finishing, coating, padding, exhausting, and spraying can be used to apply the formulation of the present invention to a textile material. Among all the options of application methods, padding is the preferred application method of the invention.

Depending upon the concentration of the alumina in the formulation of the present invention, the targeted add on level of the alumina on the textile materials, and wet pick up of the padding process set up, the alumina formulation of the present invention may need to be diluted first before a padding process.

The alumina formulation concentration C in a pad bath can be calculated with the following equation:

$$C = \frac{A}{W \times B}$$

where
A is the targeted add on level of alumina,
W is the wet pick up, and
B is the alumina concentration in the alumina formulation.

For example, if the concentration of the alumina formulation is 20% based on weight of alumina formulation, the wet pick up at the time of the padding application is 80%, and the add on level of alumina is targeted at 0.64% of alumina based on the weight of dry textile material, the alumina formulation concentration C in the pad bath should be:

$$C = \frac{0.64}{0.8 \times 0.2} = 4\%$$

Once the padding bath is made up, the bath is fed into a padding trough and the padding operation is initiated straightaway. Following the padding operation, the wet fabric is dried in a tenter curing range. The curing or drying temperature useful for the present invention should be in the range of 80 C to 200 C, preferably in a range of 90 C to 190 C, and more preferably in a range of 120 C to 180 C.

The add on level of the alumina in a textile material in accordance with aspects of this invention is in a range of 0.05% to 20% based on the weight of dry textile material. Preferably, the add on level is in a range of 0.5% to 10%. The most preferable alumina use level range is in a range of 0.1% to 2% based on weight of dry textile material.

In another aspect of the invention, the alumina is cured in order to provide satisfactory durable odor capturing property to a textile material. An example of a curing temperature suitable for use in the present invention is at or above 80 C, preferably higher than 90 C, and more preferably above 120 C. Such treated textile materials were found to improve significantly on its ability to absorb unpleasant odors such as isovaleric acid and the odor capturing property of treated textile materials lasts at least 25 home launderings.

As another example of an application method, the alumina could also be incorporated into a textile fiber as it is being manufactured. In this example, alumina powder, liquid alumina dispersion, or liquid alumina solution can be incorporated into a molten polymer resin as it is being extruded into fiber form. During the process, alumina powder, liquid alumina dispersion, or liquid alumina solution is fed into an extruder along with a polymer resin. Polymers that can be used to produce fibers include, but are not limited to, polypropylene, polyethylene, nylon, and polyester. The extruder acts to melt and homogenize the polymer and any additives. The extruder mechanically breaks down alumina aggregates and disperses the alumina throughout the molten polymer. The resulting mixture is then fed through a spinneret which forms the polymer into fibrous strands. As the fibers are quenched the molten polymer solidifies to form fibers containing domains of alumina throughout.

Alumina powder or liquid forms can also be incorporated into fibers produced through a solution spinning process. Polymers suitable to solution spinning include, but are not limited to, cellulosic based materials such as viscose. In this process, alumina powder, liquid dispersion or liquid solution is mixed and dispersed into a dissolved polymer solution. The resulting mixture is forced through a spinneret to form fibrous strands that upon solidification contain domains of alumina.

Fibers, whether solution or melt spun, typically undergo further processing following fiber formulation. This can involve application of certain finishing agents that include, but are not limited to, lubricants and antistats. As another means of applying alumina to a fiber, a liquid dispersion or solution of alumina can be added into the fiber finishing process and applied along with other fiber finishing agents described herein.

Even though alumina in dry powder form or liquid dispersion or soluble form can be used alone to achieve the benefit of the present invention, other odor capturing additives can be formulated or combined together with the alumina of the present invention to broaden the spectrum of the odor capturing activity of the alumina.

The formulation of the present invention may comprise antimicrobials. Antimicrobials can be used in addition to the odor capturing formulation of the present invention to further control the odor generation of textile materials. A wide variety of antimicrobials can be used for this purpose including, but not limited to, triclosan, zinc pyrithione, metal salts and oxides, phenols, botanicals, halogens, peroxides, heterocyclic antimicrobials, quaternary ammonium compounds, aldehydes, and combinations thereof. The antimicrobials can be applied together with the alumina in one application stage either by padding or exhausting, or the two additives can be applied separately in different stages in a textile wet finishing process.

Other additives can also be incorporated in the formulation of the present invention to improve the use property of the liquid alumina formulation such as dispersibility in water, viscosity, and shelf life stability if a liquid formulation is needed to practice the current formulation. For example surfactants or dispersants or pH adjusting agents can be used to help the dispersibility or solubility of alumina in water.

Binders are not required for the invention but can be optionally used along with alumina of the invention.

The liquid carrier or media into which the alumina is added can be water or any other organic solvent or the combinations. Water is preferred.

Other agents can be optionally incorporated into the invention such as rheology modifiers, colorants, preservatives, extenders, among others.

Examples of types of textile materials that may be used in the practice of the present invention include, but are not limited to, textile materials comprised of synthetic fibers, natural fibers, or a combination thereof. Examples of textile materials include, but are not limited to, polyester, cotton, rayon, nylon, wool, polypropylene, polyurethane, acrylic, and combinations thereof. The invention also covers a wide variety of textile material construction structures such as woven and nonwoven textile structures.

EXAMPLES

A gas chromatographic method was used to determine the odor capturing property of textile materials treated with the formulation of the present invention. A textile fabric cut in 50 cm2 was placed in a sealed 500 ml Erlenmeyer flask. Five microliters of odorant solution was injected into the flask through a microsyringe. The standing time for fabric and odorant was two hours and then the odorant in the headspace gas was sampled and analyzed using a gas chromatograph to determine the percentage reduction of the odorant.

The percentages of the formulation components shown in Table 1 are based on the weight of the liquid formulation.

TABLE 1

| Components | Functionality | Form. #1 | Form. #2 | Form. #3 | Form. #4 | Form. #5 | Form. #6 |
|---|---|---|---|---|---|---|---|
| Water | Carrier | 90 | 88.5 | 80 | 75 | 60 | 79.9 |
| Citric acid | Adjusting pH, extender | 5 | 5 | 0 | 0 | 0 | |
| Urea | Adjusting pH, extender, improving colorfastnes s | 0 | 0 | 15 | 5 | 0 | |
| Dispal 23N4-80* | Capturing odor | 5 | 5 | 5 | 20 | 20 | 20 |
| Ultraphil TG** | Moisture management | | | | | 20 | |
| Microban ZO6 | Antimicrobial | | 1.5 | | | 0 | |
| Kathon CG/ICP | In can preservative | | | | | | 0.1 |

*Trade mark of Sasol
**Trade mark of Huntsman Corporation

Treatment

A Mathis lab padder model HF-350 was used to treat a textile fabric with the alumina formulation for the purpose of illustration. The textile fabric information is listed in the following Table 2. These formulations were diluted first in water to make up the pad bath with a letdown ratio based on pre-measured wet pick up and targeted add on level of the alumina formulation on the fabric. All the add on levels of the formulations listed in Table 2 is based on the weight of dry fabric. Immediately following the padding, the fabric was dried and cured in a Mathis lab LTE infrared drier. The treated fabrics along with untreated control fabrics were laundered using a Whirlpool top loader washing machine and Tide detergent.

TABLE 2

| | Add on level | Fabric | Curing condition |
|---|---|---|---|
| Treatment Form. #1 | 5% | Dyed Polyester Fabric* | 150 C. for 45 seconds |
| Treatment Form. #2 | 5% | Undyed Polyester Fabric | 150 C. for 45 seconds |
| Treatment Form. #3 | 5% | Polyester Fabric | 130 C. for 45 seconds |
| Treatment Form. #4 | 3% | Polyester Fabric | 130 C. for 45 seconds |
| Treatment Form. #5 | 3% | Polyester Fabric | 130 C.for 45 seconds |
| Treatment Form. #6 | 3% | Polyester Fabric | 130 C. for 45 seconds |
| Control 1 | NA | Dye Polyester Fabric | NA |
| Control 2 | NA | Undyed Polyester Fabric | NA |
| Control 3 | NA | Polyester Fabric | NA |
| Control 4 | NA | Polyester Fabric | NA |
| Control 5 | NA | Polyester Fabric | NA |
| Control 6 | NA | Polyester Fabric | NA |

*A 100% polyester knit fabric was dyed with 0.05% Disperse Blue 56 along with 2.5% Ultraphil TG and 0.3% Microban ZO6.

Isovaleric Acid Reduction

TABLE 3

| | Isovaleric acid reduction (%) | | | Isovaleric acid reduction (%) | |
|---|---|---|---|---|---|
| Formulation | No home laundry | 10 home laundries | Controls | No home laundry | 10 home laundries |
| Form #1 | 35.0 | 63.0 | Control 1 | 27.0 | 34.0 |
| Form #2 | 79.0 | 64.0 | Control 2 | 10.0 | 9.0 |
| Form #3 | 89.5 | 79.4 | Control 3 | 20.8 | 20.7 |
| Form #4 | 95.9 | 94.0 | Control 4 | 38.5 | 52.7 |

TABLE 3-continued

| | Isovaleric acid reduction (%) | | | Isovaleric acid reduction (%) | |
|---|---|---|---|---|---|
| Formulation | No home laundry | 10 home laundries | Controls | No home laundry | 10 home laundries |
| Form #5 | 93.4 | 86.5 | Control 5 | 38.5 | 52.7 |
| Form #6 | 95.7 | 93.3 | Control 6 | 28.0 | 19.0 |

A comparative example is provided below comparing performance of boehmite as compared with an activated alumina for odor capture.

Odor Capture Performance—Isovaleric Acid (IVA):

TABLE 4

| Liquid Dispersion Formulation | Application Level | Fabric Type | 0 HL | 25 HL |
|---|---|---|---|---|
| Untreated Control | N/A | 100% polyester knit | 79% | 75% |
| Boehmite formulation | 3% | 100% polyester knit | 94% | 87% |
| Activated alumina - basic (20%) | 3% | 100% polyester knit | 83% | 73% |
| Activated alumina - neutral (20%) | 3% | 100% polyester knit | 80% | 75% |
| Activated alumina - acidic (20%) | 3% | 100% polyester knit | 80% | 76% |

Activated alumina (aluminum oxide) were obtained from Sigma-Aldrich designated under Product numbers 199443, 199974, and 199966, respectively.

Boehmite used in the boehmite formulation was obtained from Sasol under trade name DISPAL® 23N4-80.

All the formulations were made by dispersing the powder active materials in water to make a 20% active aqueous formulation.

Application Procedure:

(1) 20% active formulation was diluted to 3% with water to make pad bath. (2) Pad bath was then padded onto the fabric using a lab scale textile padding machine. (3) The padded fabric was dried and cured in an IR drier at 150° C. for 45 seconds. The fabrics used were electrostatically neutral. (4) For fabrics with home laundering, a home top load washing machine was used for the laundry and Tide was used as the detergent.

The results unexpectedly showed the superior performance of boehmite formulation as compared to the activated alumina. It was surprising that not only did boehmite work for this purpose but that it also worked much better than aluminium oxide as the pore volume in aluminum oxide is much greater than boehmite.

In the present invention, it was surprisingly found that water dispersible alumina, particularly boehmite, provides a remarkable durable odor capturing property to a textile material without the use of a binder or a cross-linker. It is well known or widely accepted in the industry that a binder or a cross-linker should be used along with an active odor capturing agent in textile odor finishing treatment in order to achieve durable effect. A binder is even more desirable if the odor capturing agent is particulate and inorganic in nature. In the present invention, it was unexpectedly found that water dispersible alumina without the use of a binder or a cross-linker not only imparts an initial odor capturing property to a textile material but also imparts to the textile material a durable effect to withstand multiple laundries without use of a binder or a cross-linker. It was also surprisingly found to be particularly effective with polyester fibers and textiles as opposed to other materials.

As used herein, the terms "comprise," "comprising," "include," and "including" are intended to be open, non-limiting terms, unless the contrary is expressly indicated.

As used herein, the terms "composition" and "formulation" are intended to encompass mixtures or solutions having two or more components. These terms are not limiting as to the precise form of solution (e.g. simple solution, suspension, dispersion, colloid), and one of ordinary skill in the relevant art will appreciate that various forms may be employed without departing from the inventive concepts disclosed herein.

As used herein, the term "textile material" is intended to be a general term encompassing fibers, yarn intermediates, yarn, fabrics, and products or articles made from fabrics that retain more or less completely the strength, flexibility, and other typical properties of the original fiber or filaments.

As used herein, the terms "biocidal" and like are intended to convey activity against biocidal, antibacterial, antifungal, anti-algae, antiviral, and other pathogenic organisms. The broad biocidal spectrum includes Gram-positive and Gram-negative bacteria, spore and non-spore forming bacteria, viruses, vegetative and non-vegetative fungi, yeast, protozoa, and other microorganisms.

Biocidal activity is intended to mean an inhibiting effect on microbes. Such effects may range from cidal (killing a significant percentage of microbes within a given time period) to static (preventing proliferation, yet not necessarily killing a substantial fraction).

Unless otherwise noted, weight percent (wt. %) is herein expressed as a percent of the total weight of the textile substrate to be treated.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

What is claimed is:

1. An odor absorbing article comprising:
    a textile material that is electrostatically neutral; and
    an odor capturing formulation, directly applied to the textile material through padding or exhaustion and aggregated within pores of the textile material, the odor capturing formulation comprising a liquid dispersible non-fibrous boehmite without a binder or a cross-linker;
    wherein concentration of the non-fibrous boehmite without the binder or the cross-linker ranges from 0.05% to 20% based on a weight of dry textile material;

wherein the non-fibrous boehmite without the binder or the cross-linker has a dispersed particle size ranging from 50 nm to 100 nm.

2. The article according to claim 1, wherein the odor capturing formulation further comprises a component selected from the group consisting of surfactant, dispersant, pH adjusting agent, antimicrobial, and a combination thereof.

3. The article according to claim 1, wherein the synthetic non-fibrous boehmite without the binder or the cross-linker has a crystalline structure.

4. The article according to claim 1, wherein the textile material exhibits four-fold higher isovaleric acid reduction properties for a predetermined number of launderings when compared to an untreated textile material.

5. The article according to claim 4, wherein the predetermined number of launderings is twenty-five.

6. The article according to claim 1, wherein the article reduces isovaleric acid by 79% or greater.

7. The article according to claim 1, wherein the article reduces isovaleric acid by 89% or greater.

8. The article according to claim 1, wherein the article reduces isovaleric acid by 95% or greater.

9. The article according to claim 6, wherein the article reduces isovaleric acid by 64% or greater after twenty-five home launderings.

10. The article according to claim 7, wherein the article reduces isovaleric acid by 79% or greater after twenty-five home launderings.

11. The article according to claim 8, wherein the article reduces isovaleric acid by 86% or greater after twenty-five home launderings.

12. The article according to claim 1, wherein the odor capturing formulation is dried at a temperature at or above 120° C.

13. An odor absorbing article comprising:
a textile material that is electrostatically neutral; and
an odor capturing formulation, directly applied to the textile material through padding or exhaustion and aggregated within pores of the textile material, the odor capturing formulation comprising a liquid dispersible non-fibrous boehmite without a binder or a cross-linker and an antimicrobial;
wherein concentration of the non-fibrous boehmite without the binder or the cross-linker ranges from 0.05% to 20% based on a weight of dry textile material;
wherein the non-fibrous boehmite without the binder or the cross-linker has a dispersed particle size ranging from 50 nm to 100 nm.

14. The article according to claim 13, wherein the antimicrobial is selected from the group consisting of triclosan, zinc pyrithione, metal salts and oxides, phenols, botanicals, halogens, peroxides, heterocyclic antimicrobials, quaternary ammonium compounds, aldehydes, and combinations thereof.

15. The article according to claim 13, wherein the textile material exhibits four-fold higher isovaleric acid reduction properties for a predetermined number of launderings when compared to an untreated textile material.

16. The article according to claim 13, wherein the odor capturing formulation is dried at a temperature at or above 120° C.

17. An odor absorbing article comprising a textile material and an odor capturing formulation, the odor absorbing article formed by the steps of:
directly applying the odor capturing formulation to the textile material through padding or exhaustion, the odor capturing formulation comprising a liquid dispersible, non-fibrous boehmite without a binder or a cross-linker,
drying the textile material having the odor control formulation directly applied thereon at a temperature at or above 120° C., and
aggregating the non-fibrous boehmite without the binder or the cross-linker together within pores of the textile material, while drying the textile material, thereby forming a textile material having odor reduction properties,
wherein concentration of the non-fibrous boehmite without the binder or the cross-linker ranges from 0.05% to 20% based on a weight of dry textile material,
wherein the non-fibrous boehmite without the binder of the cross-linker has a dispersed particle size ranging from 50 nm to 100 nm, and
wherein the textile material is electrostatically neutral.

18. The article according to claim 17, wherein the odor capturing formulation further comprises a component selected from the group consisting of surfactant, dispersant, pH adjusting agent, antimicrobial, and a combination thereof.

19. The article according to claim 17, wherein the article exhibits four-fold higher isovaleric acid reduction properties for a predetermined number of launderings when compared to an untreated article.

* * * * *